(12) United States Patent
Macklin et al.

(10) Patent No.: US 7,677,449 B2
(45) Date of Patent: Mar. 16, 2010

(54) AUTOMATIC INTEGRATED SENSING AND ACCESS CONTROL

(75) Inventors: Jon D. Macklin, National City, CA (US); Walter C. Bonneau, Jr., Escondido, CA (US); Bruce D. Roberts, San Diego, CA (US)

(73) Assignee: Cubic Corporation, San Diego, CA (US)

( * ) Notice: Subject to any disclaimer, the term of this patent is extended or adjusted under 35 U.S.C. 154(b) by 147 days.

(21) Appl. No.: 12/062,390

(22) Filed: Apr. 3, 2008

(65) Prior Publication Data

US 2009/0166412 A1 Jul. 2, 2009

Related U.S. Application Data

(63) Continuation of application No. 11/329,640, filed on Jan. 11, 2006, now Pat. No. 7,367,494.

(60) Provisional application No. 60/659,830, filed on Mar. 8, 2005.

(51) Int. Cl.
*G06K 5/00* (2006.01)

(52) U.S. Cl. .................. 235/382; 235/380; 235/383; 235/384; 705/5; 705/13

(58) Field of Classification Search .......... 235/380, 235/382, 383, 384; 705/5, 13
See application file for complete search history.

(56) References Cited

U.S. PATENT DOCUMENTS

| | | | |
|---|---|---|---|
| 4,821,118 A | 4/1989 | Lafreniere et al. | |
| 5,200,614 A | 4/1993 | Jenkins | |
| 5,491,326 A | 2/1996 | Marceau et al. | |
| 5,491,337 A | 2/1996 | Jenkins et al. | |
| 5,741,984 A | 4/1998 | Danylewych-May et al. | |
| 6,073,499 A | 6/2000 | Settles | |
| 6,765,198 B2 | 7/2004 | Jenkins et al. | |
| 6,975,227 B1 | 12/2005 | Nishikawa et al. | |
| 7,047,829 B2 | 5/2006 | Napoli | |
| 7,139,406 B2 | 11/2006 | McClelland et al. | |
| 2003/0128099 A1 | 7/2003 | Cockerham | |
| 2004/0073439 A1 | 4/2004 | Shuster | |
| 2004/0165750 A1 | 8/2004 | Chew | |
| 2004/0169076 A1 | 9/2004 | Beale et al. | |
| 2005/0019220 A1 | 1/2005 | Napoli | |
| 2005/0288937 A1 | 12/2005 | Verdiramo | |
| 2006/0180647 A1 | 8/2006 | Hansen | |

FOREIGN PATENT DOCUMENTS

| | | |
|---|---|---|
| EP | 0599291 A2 | 6/1994 |
| EP | 1182622 A1 | 2/2002 |
| WO | WO03/075119 A2 | 9/2003 |

*Primary Examiner*—Allyson N Trail
(74) *Attorney, Agent, or Firm*—Townsend and Townsend and Crew, LLP

(57) ABSTRACT

An access control system for sensing exposure to items of interest for a person associated with a unique identifier of a fare card or ticket is disclosed. The access control system includes the unique identifier, an exposure detector and a processor. The unique identifier associated with the person that is flagged when exposure is detected. The exposure detector detects exposure to items of interest by the person. The processor is coupled to the exposure detector. The message is communicated away from the processor to a remote location when the unique identifier is flagged.

24 Claims, 5 Drawing Sheets

AUTOMATIC INTEGRATED SENSING AND ACCESS CONTROL

This application is a continuation of U.S. patent application Ser. No. 11/329,640, filed Jan. 11, 2006, which claims the benefit of U.S. Provisional Application No. 60/659,830 filed on Mar. 8, 2005, each of which is hereby incorporated by reference herein in its entirety.

BACKGROUND

This disclosure relates in general to securing controlled areas and, but not by way of limitation, to automatic security systems used for controlled areas.

There are terrorism concerns in many contexts. Situations where people congregate have become attractive targets for those who plant bombs. Terrorists often rely upon forged authentication documents such that knowing true identities is not possible. Additionally, terrorists seek out situations where they can anonymously gain access to large amounts of people to increase the impact of their bombs.

Airports have a long history of controlling access by persons with certain items that could aid hijacking an airplane. For example, airports have security checkpoints where metal detectors are used on people and carry-on bags are searched. Some airports use X-ray machines on bags and chemical detectors on bags and people. These systems interrogate a bag or person without knowing the identity of the person being interrogated.

Security systems are used to secure areas. Things such as security codes, biometric information and/or identity cards are used to authenticate a person before authorizing entry to the secure area. In these circumstances, a known person is authenticated by way of the information provided. For example, a new person is added to the database of allowed persons along with the code from their identity card. When the identity card is provided, the person is allowed entry to the secured area.

Transit systems have been the subject of terrorist incidents. Suicide bombers have carried bombs into buses or trains. Additionally, bombs have been left in public transport by terrorists. Increased foot patrols have been used for transit systems to increase the likelihood of apprehending terrorists or bombs they have left behind. In some cases, canine officers are used to try to find those carrying explosives or the explosives themselves.

SUMMARY

In one embodiment, the present disclosure provides an access control system for sensing exposure to items of interest for a person associated with a unique identifier of a fare card or ticket. The access control system includes the unique identifier, an exposure detector and a processor. The unique identifier associated with the person that is flagged when exposure is detected. The exposure detector detects exposure to items of interest by the person. The processor is coupled to the exposure detector. The message is communicated away from the processor to a remote location when the unique identifier is flagged.

In another embodiment, the present disclosure provides an access control system for sensing exposure to items of interest for a person associated with an identifier that is machine-readable from a media. The access control system including an identifier, an exposure detector and a processor. The identifier associated with a person. The exposure detector detects exposure to items of interest by the person. The processor coupled to the exposure detector. When exposure is detected, the identifier is flagged and a message is communicated away from the processor to a remote location. The identifier is recognized at an access control point, where access beyond the access control point can be controlled.

In yet another embodiment, the present disclosure provides a method for flagging a person associated with a machine-readable identifier based, at least in part, upon exposure to at least one predetermined item. In one step, the identifier, associated with the person, is recognized. The identifier corresponds with a card or ticket. The person is tested for exposure to at least one predetermined item. A point away from the testing of the identifier is notified of an outcome of the testing step.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

Figure 1:
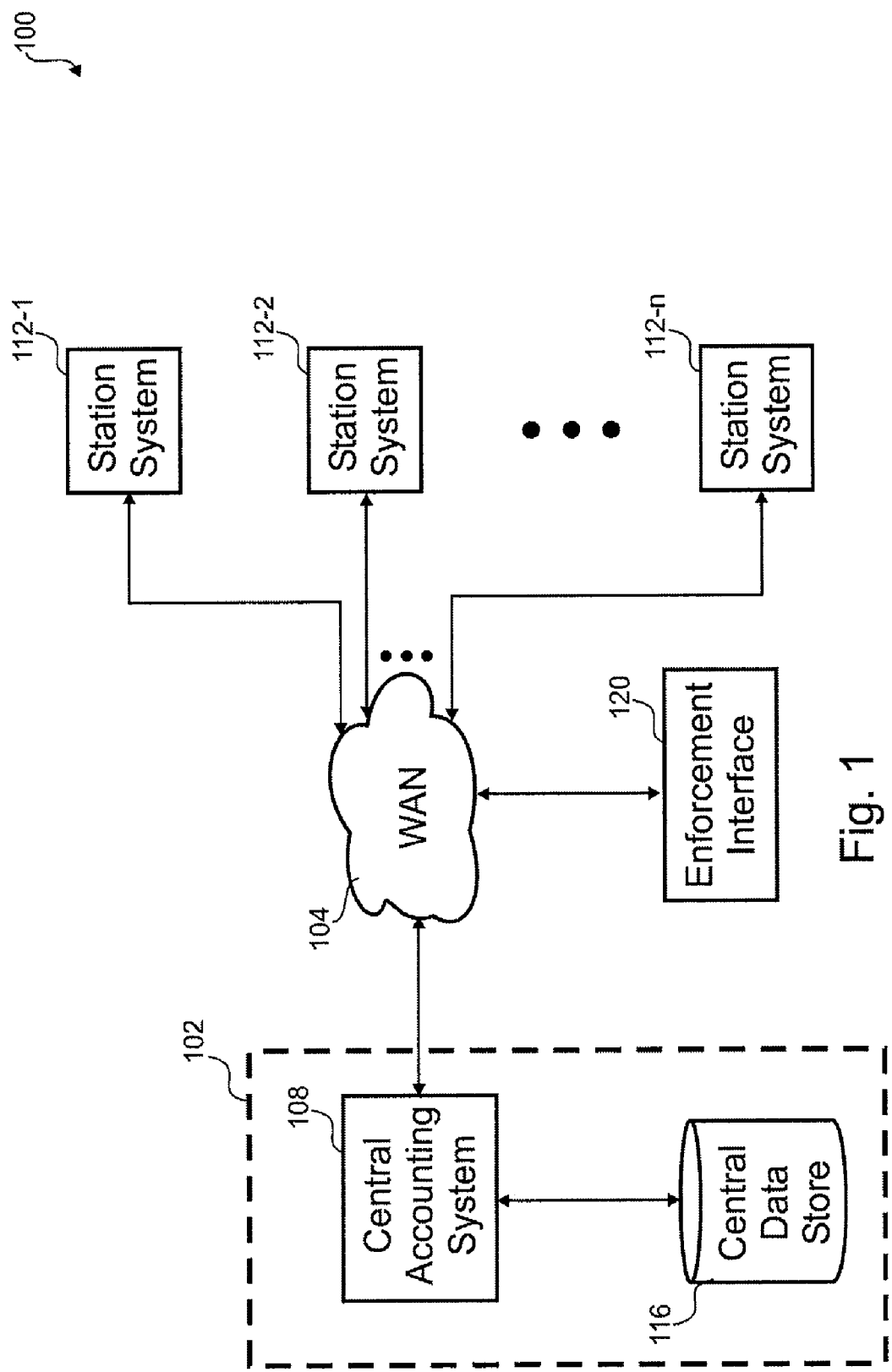
FIG. 1 is a block diagram of an embodiment of a transit fare system.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It being understood that various changes may be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Referring first to FIG. 1, a block diagram of an embodiment of a transit fare system 100 is shown. This embodiment is in the context of the transit fare system 100, which is a closed system where fare cards have a stored value and serial number associated with the card. In one embodiment, a contactless smart card is used for the fare card, but other embodiments could use serialized magnetic stripe cards, digital tokens, RFID tags, cell phone payment, government-issued identity cards, smart cards with contacts, or any other portable device or card that has a unique identifier generally associated with a person. The user can add an amount or credit to the far card to allow further use in the transit fare system 100. The credits, debits and stored value can include a monetary credit, a usage credit and/or a usage period. A number of station systems 112 are distributed across the transit fare system 100 and generally correspond to the transit stations where the fare card might be used.

There is a central control system 102 that communicates with the various station systems 112 using a wide area network (WAN) 104 that may be public or private. The WAN 104 could be packet switched or circuit switched connections using telephone lines, coaxial cable, optical fiber, wireless communication, satellite links, and/or other mechanisms for communication. Communication between the station systems 112 and the central control system 102 may be in real time or periodic. Usage of fare cards throughout the transit system 100 can be tracked. Additionally, sensed exposure to items of interest, photos and biometrics can be gathered throughout the station systems 112 and stored in the central data store 116. Fare cards can be flagged by one station system 112-1 and passed to another station system 112-2 by way of the central control system 102.

The central control system 102 could have many more components, but only the components related to controlling access according to exposure to items of interest. When exposure is sensed at any of the station systems 112, the central control system 102 can notify appropriate authorities through a law enforcement interface 120. The fare cards associated with persons who are likely to have been exposed to items of interest are flagged. The station systems 112 can be notified to prevent access and/or alert local police officers when the fare card is encountered. In some embodiments, fare cards with RFID tags can be read as a holder passes throughout the transit system 100. A flagged fare card can be tracked wherever used or sensed within the system 100.

In this embodiment, a central accounting system 108 and a central data store 116 are shown for the central control system 102. The central accounting system 108 receives periodic reports upon how credits or debits are being processed throughout the system 100. Additionally, any sensed items of interest are transmitted to the central accounting system 108 in an alert message. The alert message may also be sent the station computer, other stations, law enforcement, etc.

Table I shows an example of the alert message resulting from a sensed exposure of a card holder to an item of interest and data fusion. Data fusion is the accumulation of different types of information to make an intelligent decision for a particular transaction. In this example, a particular fare card is associated with a holder where nitrates were sensed at a particular time and date. The machine number could correspond to a vending machine, turnstile, or other machine that can sense the fare card serial number and an item of interest. A captured video clip of the holder is sent to the central data store 116.

TABLE I

Alert Message/Data Fusion Example

| Field | Example |
|---|---|
| Machine Number | 34sd82k |
| Encounter Date | Jul. 21, 2008 |
| Encounter Time | 21:32:05 |
| Fare Card Serial Number | 23490782 |
| Transaction Location | Fare Load |
| Transaction Type | Cash |
| Captured Info | Video |
| Sensed Item | Nitrates |
| Flag Status | Flagged |

In another embodiment shown in Table II, another example of a fare card is shown where the holder is cleared for certain sensed items after data fusion. A turnstile (i.e., machine number 99k8645a) may have read the fare card (serial number 23489202) and sensed gun powder. In this case, the fare card is associated with a law enforcement officer in the data fusion process such that sensing gun powder from a weapon is found to be not unusual and does not result in flagging. Even though a picture is captured, the holder is cleared such that it may not be retained. The transit system 100 could still track the holder to know where the law enforcement officer is located.

TABLE II

Alert Message/Data Fusion Example

| Field | Example |
|---|---|
| Machine Number | 99k8645a |
| Transaction Date | Sep. 28, 2006 |
| Transaction Time | 00:02:05 |

TABLE II-continued

Alert Message/Data Fusion Example

| Field | Example |
| --- | --- |
| Fare Card Serial Number | 23489202 |
| Transaction Location | Turnstyle |
| Transaction Type | Debit Card |
| Captured Info | Photo |
| Sensed Item | Explosives |
| Flag Status | Cleared |

These items listed in Tables I and II are an example of some of the items that can be used in the data fusion process that may allow a more intelligent decision than any of the items taken by themselves. Additionally, usage history of the fare card, past detection of items of interest, past transactions, security alerts, and any identity information (e.g., credit card information), could also be used along with information gathered from the present transaction in determining whether a fare card should be flagged.

The central accounting system 108 receives all these alert messages and updates a record for each fare card in the central data store 116. Subsequent system 100 interaction with the fare card that has an alert message results in the transit fare system 100 sending a further alert message. In addition to the central accounting system 108, the station system 112 may alert officers and other machines to the card holder of interest.

The central control system 102 and/or station systems can perform data mining on fare cards and tickets stored in their systems. Where a credit card or government issued identification is associated with a fare card or ticket, information from previous transactions and other information can be stored to take advantage of the data fusion to increase accuracy in eliminating false negatives and positives. For example, traces of nitrates found for the tenth time on a farmer could eliminate further alerts when nitrates are sensed on that same card holder. In another example, cash purchases of expensive tickets could be more prone to alert if something is sensed under the presumption that a terrorist may be more likely to pay in cash. Tickets purchased at the same time can be tied together such that if one is flagged by an alert, all could be flagged.

Figure 2:
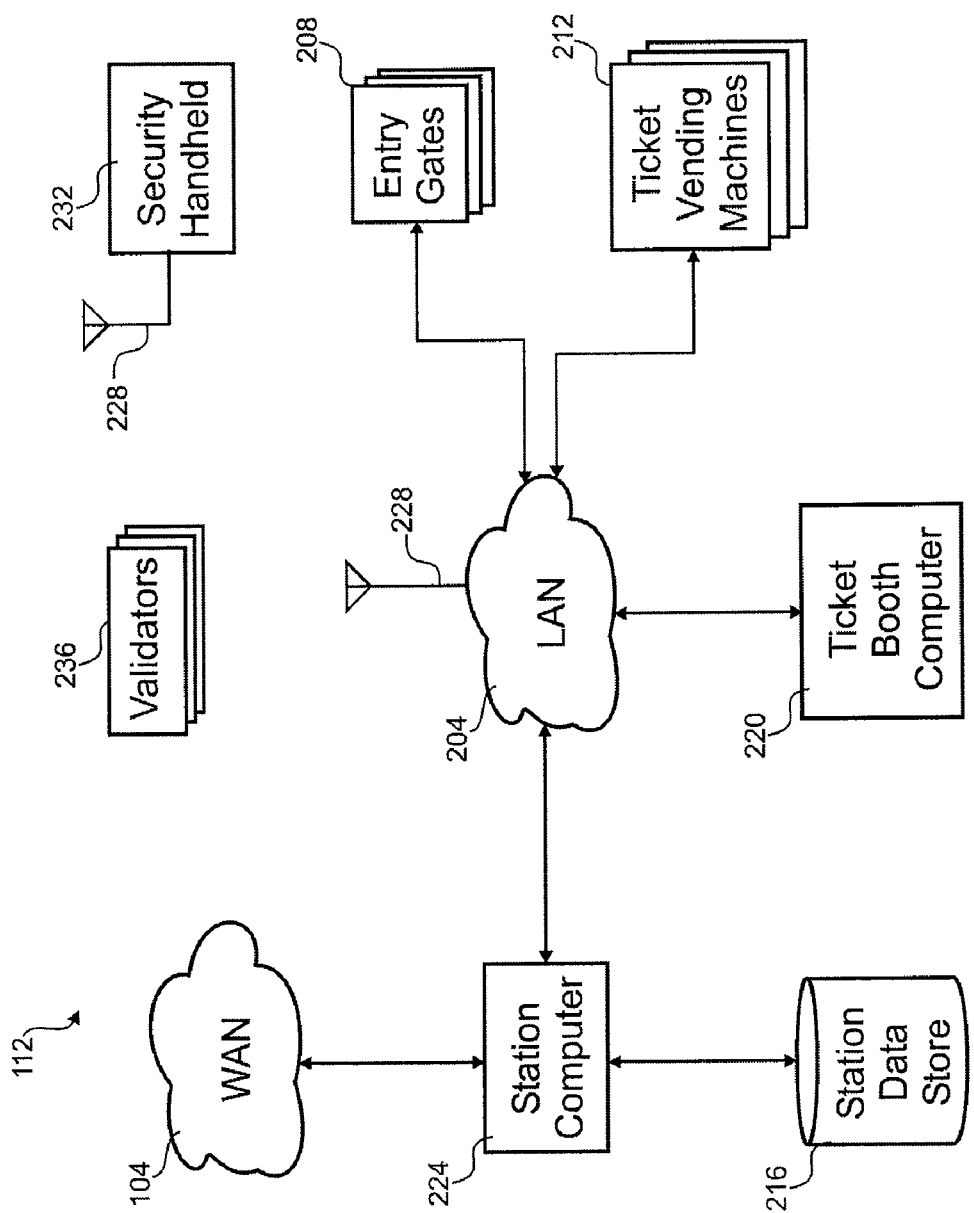
FIG. 2 is a block diagram of an embodiment of a transit station system.

With reference to FIG. 2, a block diagram of an embodiment of a transit station system 112 is shown. Various transit stations may have some or all of the components shown in the block diagram. A local area network (LAN) 204 couples the various systems together and could include point-to-point connections, packet switched connections, wireless connections, and/or other networking techniques.

A station computer 224 is coupled to the WAN 104 to allow communication with the central accounting system 108. Processing of local information is performed on the station computer 224. For example, video surveillance for the station could be accessible from the station computer along with transit schedule information. Alert messages could be routed by the station computer 224 to the central accounting system 108 and other places within the station. Some embodiments could track a card associated with a holder where exposure to an item of interest was detected. This could include RFID sensing, video surveillance, encounters a turnstiles and ticket counters.

A station data store 216 stores various information used by the station system 112. Alert messages and black listed fare card serial messages are stored in the station data store 216. A ticket booth computer 220, entry gates 208, and TVMs 212 all communicate with the central accounting system 108 through the station computer 224. Some embodiments refer back to the central accounting system 108 for alerts for a particular fare card during an encounter. Other embodiments store fare card serial numbers in the station data store 216, which could be updated on a regular basis to reflect other encounters throughout the transit system 100. Any captured video, pictures and/or audio for a holder of interest could also be held on the station data store 216.

In this embodiment, the entry gates 208, ticket booths and TVMs 212 can determine transaction type (e.g., credit, debit or cash), a serial number of the card and sense exposure to items of interest. Other embodiments could have sensing stations that sense the serial number of the card with RFID and sense for exposure to items of interest from an air current or plume that passes over the holder. When an entry gate 208, ticket booth or TVMs 212 triggers on exposure to an item of interest, an alert message is sent to the station computer 224 for distribution within the station and possibly throughout the transit fare system 100. For example, the card holder may approach a human ticket vendor to purchase a ticket. The card holder could be sensed and any ticket(s) purchased could be flagged in an alert message as being associated with the card holder.

In some embodiments, the entry gate 208 could serve to prohibit entry to a holder associated with an alert. The entry gate 208 could have received an alert message or produced its own alert message for a card holder. An error message, such as "invalid ticket," could be produced on the entry gate 208 when entry fails such that a holder would likely go to a ticket booth to straiten-out the problem. In some embodiments, a silent alarm could be used such that the card holder is passed by the entry gate 208, but flagged for remedial action.

Security handhelds 232 wirelessly communicate through antennas 228 using the LAN. Other embodiments could also include wired security handhelds 232. Ticket booth computers 220 also communicate with the LAN 204. Transit workers and security officers could each have one of these ticket booth computers 220 or security handhelds 232 to receive alert messages. For example, when a TVM 212 senses that a holder was exposed to an item of interest, the alert message is sent to the station computer 224 and relayed to the security handhelds 228 and ticket booth computers 220. A user of these computers 220, 228 can pull up pictures, video and sound stored in the station data store. Any tracking of the card holder could be updated on the computer 220, 228 to allow a coordinated response to the alert situation.

In transit systems 100, there are often card validators 236 that are wirelessly or periodically connected to the station computer. For example, these validators 236 could be bar code readers held by train conductors or at the entrance to busses. These validators 236 could also perform sensing for exposure to items of interest and produce alert messages. The conductor or bus driver could be notified of an alert message produced for a card holder even if there is no current communication with the station computer 224. In various embodiments, the items of interest could include chemical compounds, nuclear materials, radiological material, biological agents, and/or explosives.

Figure 3:
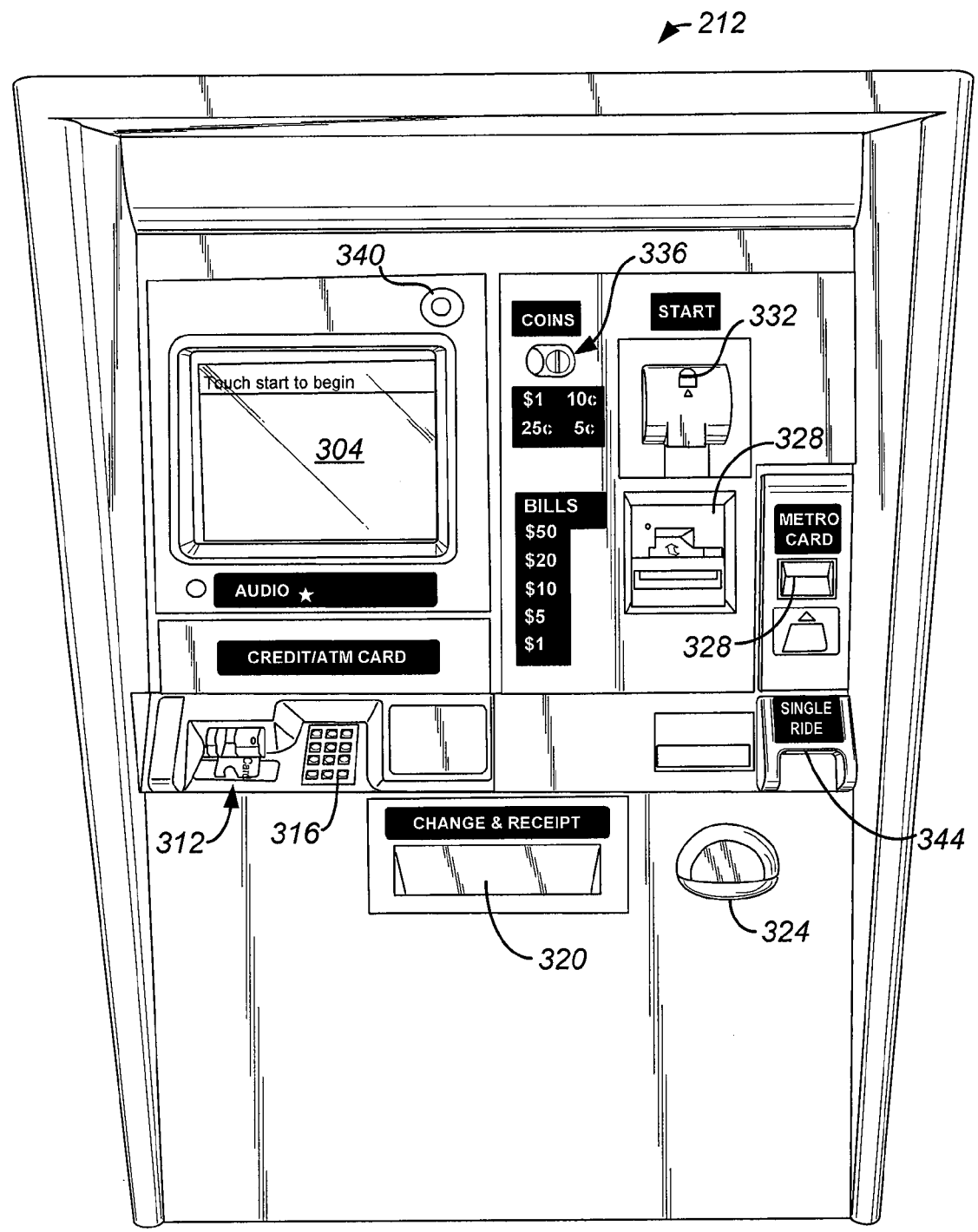
FIG. 3 depicts a perspective view of an embodiment of a ticket vending machine.
Figure 4:
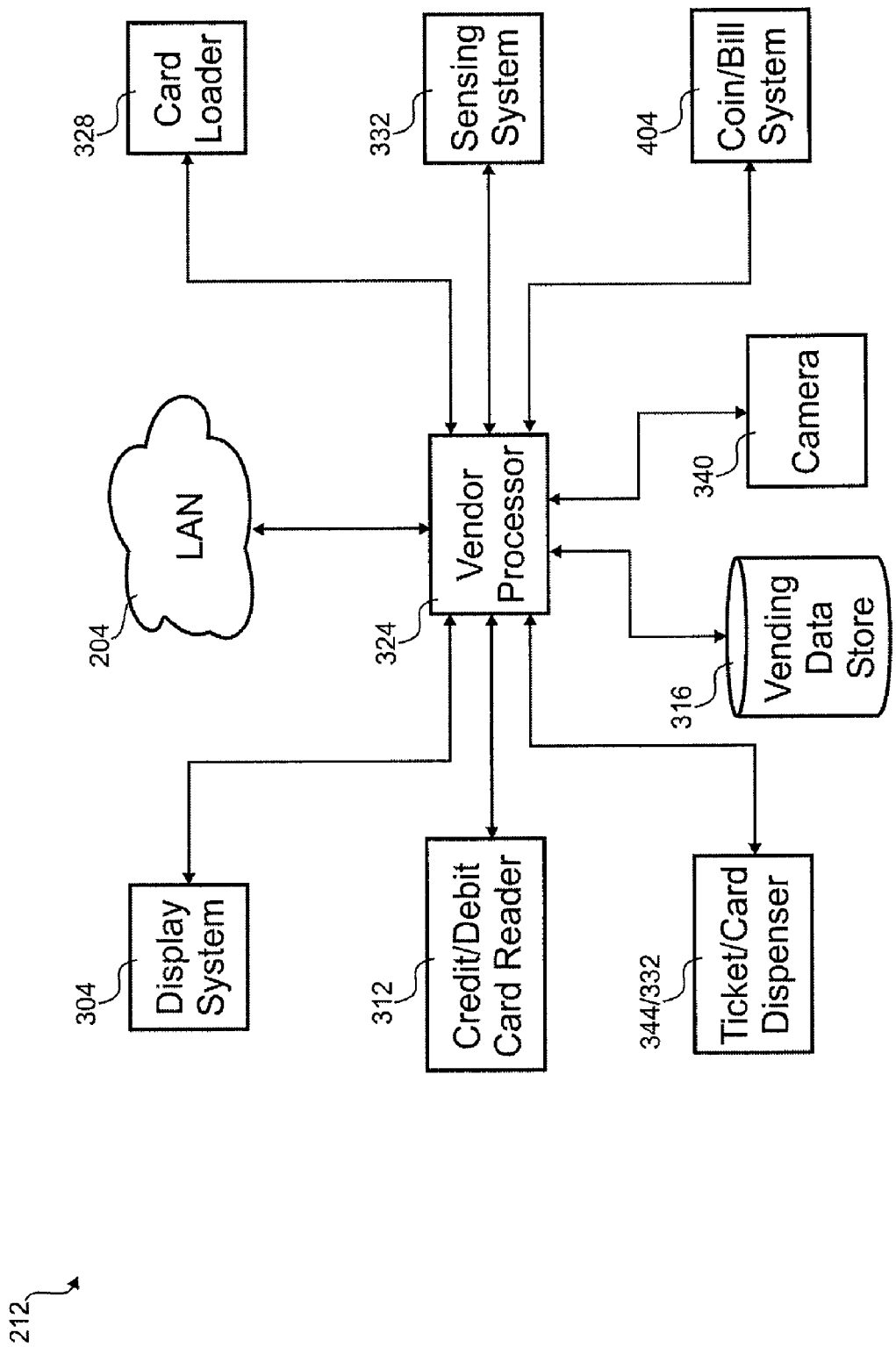
FIG. 4 is a block diagram of an embodiment of the ticket vending machine.

Referring next to FIGS. 3 and 4, a perspective view and block diagram of an embodiment of a ticket vending machine 212 are shown. Tickets and fare cards can be purchased and/or recharged at the ticket vending machine 212. A coin/bill system 404 and credit/debit card reader 312 are used to input value to purchase more fares and credits. A coin slot 336 and bill loader 328 are used to accept cash. Change is along with a receipt in a change/receipt slot 320 and coin return 324. A pin pad 316 is provided adjacent to the credit/debit card reader to enter numerical information such as a pin code for a debit card.

A display system 304 prompts the card holder through the refill/purchase process. For example, the screen prompts the purchaser to touch the start pad 332 to begin the process. A serialized card can be input into a recharge slot 328 or a new card issued. Single ride tickets can be issued through another slot 344. Whenever the holder enters something into the ticket vending machine 212, it can be tested for exposure to an item of interest. For example, credit/debit cards, serialized card for recharge, bills, and coins can all be tested for residue by the ticket vending machine. As is well known, the money supply can be contaminated by certain chemicals such that an alert might not be triggered, but radiation sensed on the money could trigger an alert.

In this embodiment, the start pad 332 is tied to an ion mass spectrum device that can detect exposure to chemical, biological and/or explosives. Other embodiments could use an air flow to detect residue from a plume emanating from the card holder. Some embodiments could detect residue from the holder's interaction with a touch screen over the display. Any contact or plume that can be tied to the card holder can be analyzed.

Some embodiments use biometric matching to identify the card holder. Where a biometric is matched, the serial number of the card or ticket can be tied to the biometric. For example, the start pad 332 may do fingerprint analysis. A video or still camera 340 could do facial recognition. Any biometric information can assist the data fusion process.

The video or still camera 340 can record picture(s) of the card holder. Where there is no alert, the picture(s) could be discarded after some period of time. If an alert is raised or some other level of suspicion, the captured picture(s) and any audio can be forwarded throughout the station system 112 and/or communicated with the central control system 102. Generally, all further pictures and sound capable of capture is held where a card or ticket is subject to an alert.

Figure 5:
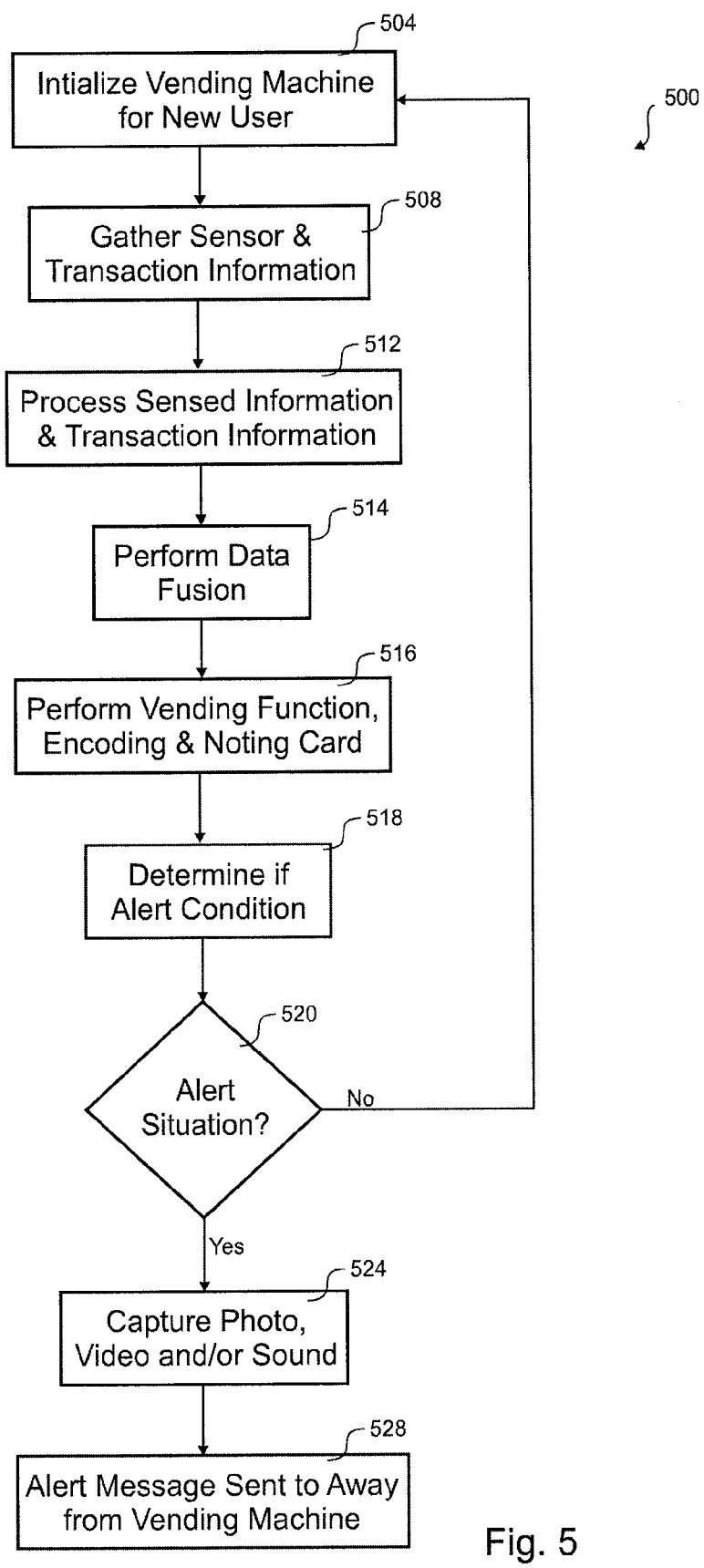
FIG. 5 is a flow diagram of an embodiment of a process for processing a card holder with sensing of exposure to items of interest.

Referring next to FIG. 5, a flow diagram of an embodiment of a process for processing a card holder is shown where there is sensing of exposure to items of interest. The depicted portion of the process begins in block 504 where the TVM 212 is configured for a new card holder. Sensor information is gathered in block 508. The sensor information could be from cards, money, touch of the card holder, plume from the card holder, and/or non-touch radiological sensing. Additionally, transaction information is gathered in step 508 such as credit/debit card, type of fare, amount, etc. The gathered information is processed in block 512, which may involve assigning a new unique identifier to a new fare card. Data fusion is performed in block 514 to determine if there has likely been exposure to an item of interest. Block 514 may use various information gathered by the TVM 212 in this transaction, but could also query the station computer 224 for additional information, could query the central control system 102, credit/debit clearing databases, and/or law enforcement or governmental databases.

In block 516, the vending function is performed to recharge or issue a card or ticket. The card or ticket has a unique serial number unique associated with it that can be attributed to the holder of the card even though the identity of the holder may not be known. Purchase information, the unique identifier, transaction history, alert condition and/or other information can be encoded on the fare card in block 516. In block 518, it is determined if the card holder should be flagged with an alert based upon the data fusion and possible other factors. This analysis could be done local to the TVM 212 or could interact with the station computer 224, law enforcement systems, and/or central control system 102 in various embodiments. Some embodiments do not have real-time access to data fusion information and only determine if there was exposure or not. Other parts of the fare system 100 determine if transit employees and security officers should be notified after analysis of the data fusion. If there is no alert in block 520, processing loops back to block 504 where the TVM 212 readies for the next customer.

Where an alert situation is determined processing goes from block 520 to block 524. Photo(s), video, and/or sound is captured to document the card holder in block 524. Some embodiments temporarily store the photo(s), video and/or sound prior to the alert determination and only save that information if an alert is determined. In block 528, an alert message is sent away from the TVM 212 to the station computer 224, law enforcement, security handhelds 232, and/or central control system 102. Further analysis may be performed remotely before alerting entry gates 208, other TVMs 212, law enforcement, other stations, transit vehicle operators, security handhelds 232, and/or ticket booths. This further analysis could be done manually and/or automatically. In some cases, for example, other law enforcement is automatically and/or manually notified.

A number of variations and modifications of the disclosed embodiments can also be used. For example, the flagging of card serial numbers as being associated with a holder exposed to an item of interest need not be limited to transit systems. The serial number could be an event ticket, a government issued identity card, and/or employee badge. Non-barriered things could be given access to, for example, a train station where conductors can validate tickets and sense for exposure in addition to the vending systems.

The techniques described herein may be implemented by various means. For example, these techniques may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof.

For a software implementation, the techniques, processes and functions described herein may be implemented with modules (e.g., procedures, functions, and so on) that perform the functions described herein. The software codes may be stored in memory units and executed by processors. The memory unit may be implemented within the processor or external to the processor, in which case it can be communicatively coupled to the processor via various means as is known in the art.

Wile the principles of the disclosure have been described above in connection with specific apparatuses and methods, it is to be clearly understood that this description is made only by way of example and not as limitation on the scope of the disclosure.

What is claimed is:

1. A transportation system for sensing exposure to items of interest, the transportation system comprising:
   a unique identifier of transportation media;
   an exposure detector that detects exposure to items of interest by a person, the transportation media or payment, wherein the exposure detector senses residue of the items of interest;
   a processor coupled to the exposure detector, wherein:

the unique identifier is flagged when the exposure to items of interest is detected, a message is communicated away from the processor to a remote location when the unique identifier is flagged, a record for the unique identifier is updated in a remote system when the message is received at the remote location, the remote system is located at the remote location, and an alert condition is associated with the unique identifier when information indicative of prior involvement with items of interest is determined; and a fare gate that automatically reads the unique identifier of the transportation media and automatically analyzes the alert condition.

2. The transportation system for sensing exposure to items of interest as recited in claim 1, wherein the information indicative of prior involvement with items of interest includes at least two of the following:

usage history of a fare card, past detection of items of interest, security alerts, and any identity information.

3. The transportation system for sensing exposure to items of interest as recited in claim 1, wherein the message is used at an access control point to prevent passing the access control point.

4. The transportation system for sensing exposure to items of interest as recited in claim 1, wherein the person possesses the unique identifier.

5. The transportation system for sensing exposure to items of interest as recited in claim 1, wherein the items of interest comprise at least one of chemical compounds, nuclear materials, radiological material, biological agents, or explosives.

6. The transportation system for sensing exposure to items of interest as recited in claim 1, further comprising an image capture device that captures an image of the person.

7. The transportation system for sensing exposure to items of interest as recited in claim 1, wherein the message includes a captured digital image of the person.

8. The transportation system for sensing exposure to items of interest as recited in claim 1, wherein the identifier is associated with an access card.

9. The transportation system for sensing exposure to items of interest as recited in claim 1, wherein the identifier is a biometric read from the person.

10. The transportation system for sensing exposure to items of interest as recited in claim 1, wherein the identifier is associated with at least one of a fare card, a credit card, an identification card, a passport, a stored value card, a contactless RFID card, or a smart card.

11. The transportation system for sensing exposure to items of interest as recited in claim 1, wherein the exposure detector detects the residue of items of interest from the person's contact to an object coupled to the exposure detector.

12. The transportation system for sensing exposure to items of interest as recited in claim 11, wherein the object comprises at least one of a pin pad, a start pad, a pad, a touch screen, a bill, a coin, a serialized card, a credit card and a debit card.

13. The transportation system for sensing exposure to items of interest as recited in claim 1, wherein the exposure detector comprises an ion mass spectrum device.

14. The transportation system for sensing exposure to items of interest as recited in claim 1, wherein the transit media comprises a fare card or ticket.

15. Transportation system for sensing exposure to items of interest for a person associated with an identifier that is machine-readable from ticket media, the transportation system comprising:

the identifier of the ticket media associated with the person, the identifier being machine-readable from the ticket media;

an exposure detector that detects exposure to items of interest by the person, the ticket media or payment, wherein the exposure detector senses residue of the items of interest;

a processor coupled to the exposure detector, wherein:

the identifier is flagged when exposure is detected, a message is communicated away from the processor to a remote location when the identifier is flagged, a record for the identifier is updated in a remote system when the message is received at the remote location, the remote system is located at the remote location, and an alert condition is associated with the identifier when information indicative of prior involvement with items of interest is determined using the remote system; and an access control point that reads the identifier of the ticket media and automatically analyzes the alert condition associated with the identifier of the ticket media, whereby access beyond the access control point can be controlled.

16. The transportation system for sensing exposure to items of interest for the person associated with the identifier that is machine-readable from the ticket media as recited in claim 15, wherein the information indicative of prior involvement with items of interest includes at least two of the following:

usage history of a fare card, past detection of items of interest, security alerts, and any identity information.

17. The transportation system for sensing exposure to items of interest for the person associated with the identifier that is machine-readable from the ticket media as recited in claim 16, wherein the association between the person and the unique identifier is that the person possesses the unique identifier.

18. The transportation system for sensing exposure to items of interest for the person associated with the identifier that is machine-readable from the ticket media as recited in claim 16, wherein the identifier is unique within the access control system.

19. A method for flagging a card or ticket media used in a transportation system based, at least in part, upon exposure to at least one predetermined item, the method comprising steps of:

providing a machine-readable identifier associated with the card or ticket media;

determining if a person, the card or ticket media or payment was exposed to at least one predetermined item of interest;

flagging the machine-readable identifier when the determining step determines there was exposure to the at least one predetermined item of interest;

notifying a point away from the testing of the machine-readable identifier when the machine-readable identifier is flagged;

updating a record for the machine-readable identifier in a remote system, which is located at a remote location;

associating an alert condition with the machine-readable identifier when information indicative of prior involvement with items of interest is determined using the remote system;

automatically reading information from the card or ticket media; and automatically analyzing information for the alert condition.

20. The method for flagging the card or ticket media used in a transportation system based, at least in part, upon exposure to at least one predetermined item as recited in claim 19, wherein the information indicative of prior involvement with items of interest includes at least two of the following:

usage history of a fare card, past detection of items of interest, security alerts, and any identity information.

21. The method for flagging the card or ticket media used in a transportation system based, at least in part, upon exposure to at least one predetermined item as recited in claim 19, wherein at least two of the steps are performed by one of a validator, a fare gate, a fare box, an access gate, or a handheld.

22. The method for flagging the card or ticket media used in a transportation system based, at least in part, upon exposure to at least one predetermined item as recited in claim 19, wherein the providing step comprises a step of reading a magnetic stripe, RFID, smart card, bar code, and/or optical track of a fare card.

23. The method for flagging the card or ticket media used in a transportation system based, at least in part, upon exposure to at least one predetermined item as recited in claim 19, further comprising a step of controlling access of the person according to the outcome.

24. The method for flagging the card or ticket media used in a transportation system based, at least in part, upon exposure to at least one predetermined item as recited in claim 19, further comprising a step of capturing an image of the person, wherein the notifying step includes a step of sending the image to the point away from the testing.

* * * * *